US011523780B2

(12) United States Patent
Hornung et al.

(10) Patent No.: US 11,523,780 B2
(45) Date of Patent: Dec. 13, 2022

(54) PATIENT TABLE WITH A SUPPORT SURFACE FOR A PATIENT

(71) Applicant: Siemens Healthcare GmbH, Erlangen (DE)

(72) Inventors: Oliver Hornung, Dormitz (DE); Gregor Niewalda, Buckenhof (DE)

(73) Assignee: Siemens Healthcare GmbH, Erlangen (DE)

(*) Notice: Subject to any disclaimer, the term of this patent is extended or adjusted under 35 U.S.C. 154(b) by 277 days.

(21) Appl. No.: 16/809,914

(22) Filed: Mar. 5, 2020

(65) Prior Publication Data
US 2020/0289067 A1    Sep. 17, 2020

(30) Foreign Application Priority Data

Mar. 14, 2019    (DE) .......................... 102019203460.8

(51) Int. Cl.
*A61B 6/00*    (2006.01)
*A61B 6/04*    (2006.01)

(52) U.S. Cl.
CPC .......... *A61B 6/0442* (2013.01); *A61B 6/0487* (2020.08); *A61B 6/4441* (2013.01)

(58) Field of Classification Search
CPC ........ A61B 6/582; A61B 6/587; A61B 6/4452
See application file for complete search history.

(56) References Cited

U.S. PATENT DOCUMENTS

| 3,648,305 A | * | 3/1972 | Ersek ................... A61B 6/4283 |
| | | | 378/180 |
| 6,408,464 B1 | | 6/2002 | Weismiller et al. |
| 2012/0138065 A1 | | 6/2012 | Campagna |
| 2017/0135891 A1 | | 5/2017 | Kettner et al. |
| 2017/0216121 A1 | | 8/2017 | White |

FOREIGN PATENT DOCUMENTS

GB    2405789 B    8/2005

OTHER PUBLICATIONS

German Office Action for German Application No. 10 2019 203 460.8 dated Jan. 17, 2020.

* cited by examiner

*Primary Examiner* — Dani Fox
(74) *Attorney, Agent, or Firm* — Harness, Dickey & Pierce, P.L.C.

(57) ABSTRACT

A patient table includes a support surface for a patient. The patient table includes a first table subunit, to provide a first surface region of the support surface; a second table subunit, to provide a second surface region; and an angle unit connected thereto, to fix a position of the first table subunit relative to the second table subunit such that the first surface region is provided in a first plane and the second surface region is provided in a second plane, intersecting the first plane at an intersection angle; and such that the support surface is secured against a change of the intersection angle upon loading of the support surface by the patient. The angle unit includes at least a first coupling element, to interact functionally with a first counter-coupling element provided on the first table subunit, to releasably connect the angle unit to the first table subunit.

22 Claims, 4 Drawing Sheets

PATIENT TABLE WITH A SUPPORT SURFACE FOR A PATIENT

PRIORITY STATEMENT

The present application hereby claims priority under 35 U.S.C. § 119 to German patent application number DE 102019203460.8 filed Mar. 14, 2019, the entire contents of which are hereby incorporated herein by reference.

FIELD

Embodiments of the invention generally relate to a patient table with a support surface for a patient, a table subunit of a patient table with a support surface for a patient, a patient table system and a medical imaging facility.

BACKGROUND

X-ray imaging facilities, for example, C-arm X-ray devices or computed tomography devices or the like which are configured to acquire the body interior of a patient by way of X-ray radiation are sufficiently well known from the prior art. As a rule, a patient is positioned on a patient positioning apparatus which is positioned, in particular, in the horizontal and/or vertical direction so that the region of relevance to the examination can be acquired. For X-ray imaging in the context of operations, in particular, patient tables are required on which not only is the patient positioned substantially in a horizontal plane, but which can be brought into particular positions which orient the relevant body region as accessibly as possible and optimally for the intervention. This can include a displacement in the height, longitudinal or lateral directions. A displacement within the patient supporting surface may also be required, for example, a different inclination of various table segments or of a head or extremity holder.

As a rule, flexible adjusting capabilities are provided for an adjustment within the patient supporting surface, which comprise joints by which the table elements can be aligned relative to one another. It is usual to use joints made of metal since they have sufficiently great stability in order to maintain the selected positioning even under loading of the patient table with the patient.

It is disadvantageous, however, that metal joints are X-ray visible and lead to metal artifacts in X-ray images. It is thereby known to reduce this in the context of the image processing by way of an algorithmic metal artifact reduction. It is also known to adjust an X-ray device such that metal artifacts are reduced at relevant sites by setting a suitable projection direction and position of the radiation source, of the patient table and of the X-ray detector in relation to one another. It is further known to produce rigid table segments, in which no movement must be enabled, from X-ray invisible material, for example, plastics or fiber-reinforced plastics.

SUMMARY

At least one embodiment of the invention provides an alternative patient table which enables an adaptation of the support surface for the positioning of a patient.

Further advantageous and partly per se inventive embodiments and developments of the invention are disclosed in the claims and the description below.

At least one embodiment of the invention relates to a patient table with a support surface for a patient, comprising a first table subunit, configured to provide a first surface region of the support surface and a second table subunit, configured to provide a second surface region of the support surface. Furthermore, the patient table according to the invention comprises an angle unit connected to the first and second table subunits. The angle unit is configured to fix the position of the first table subunit relative to the second table subunit such that the first surface region is provided in a first plane and the second surface region is provided in a second plane intersecting the first plane at an intersection angle and such that the support surface is secured against a change in the intersection angle on loading of the support surface by a patient. Furthermore, the angle unit has at least one first coupling element which is configured to interact functionally with a first counter-coupling element provided on the first table subunit, so that by way thereof, the angle unit is releasably connected to the first table subunit.

At least one embodiment of the invention further relates to a table subunit of a patient table with a support surface for a patient for use with other embodiments, having a counter-coupling element and configured to provide a surface region of the support surface.

At least one embodiment of the invention further relates to a patient table system comprising a patient table according to at least one embodiment of the invention in accordance with one of the aspects described. Furthermore, the patient table system comprises a positioning apparatus with a kinematic system for the relative positioning of the first and/or the second table subunits, wherein the positioning apparatus has at least one connecting element which is configured to interact functionally with a counter-connecting element on the first and/or second table subunit so that the positioning apparatus is releasably couplable to the first and/or second table subunit and wherein the positioning apparatus is configured in the state coupled to the first table subunit and/or the second table subunit to orient the first and the second table subunits relative to one another when the releasable connection between the angle unit and the first and/or the second table subunits is released.

At least one embodiment of the invention further relates to a medical imaging facility having an X-ray device and a patient table according to at least one embodiment of the invention, wherein the X-ray device has an X-ray source and an X-ray detector positioned in a beam path of the X-ray source and wherein at least a part of the support surface of the patient table is arranged within the beam path of the X-ray source.

At least one embodiment of the invention also relates to a medical imaging facility wherein the X-ray device is a C-arm X-ray device.

At least one embodiment of the invention further relates to a patient table including a support surface for a patient, the patient table comprising:

a first table subunit, configured to provide a first surface region of the support surface;

a second table subunit, configured to provide a second surface region of the support surface; and an angle unit connected to the first table subunit and the second table subunit, configured to fix a position of the first table subunit relative to the second table subunit such that the first surface region is provided in a first plane and the second surface region is provided in a second plane, intersecting the first plane at an intersection angle, and such that the support surface is secured against a change of the intersection angle upon loading of the support surface by the patient, the angle unit including at least a first coupling element, configured to interact functionally with a first counter-coupling element provided on the first table subunit, to releasably connect at least the angle unit to the first table subunit

BRIEF DESCRIPTION OF THE DRAWINGS

The invention will now be described using example embodiments, making reference to the accompanying drawings. The illustrations in the figures are schematic, greatly simplified and not necessarily to scale. In the drawings.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a patient table with a support surface for a patient, comprising a first table subunit, configured to provide a first surface region of the support surface and a second table subunit, configured to provide a second surface region of the support surface. Furthermore, the patient table according to the invention comprises an angle unit connected to the first and second table subunits. The angle unit is configured to fix the position of the first table subunit relative to the second table subunit such that the first surface region is provided in a first plane and the second surface region is provided in a second plane intersecting the first plane at an intersection angle and such that the support surface is secured against a change in the intersection angle on loading of the support surface by a patient. Furthermore, the angle unit has at least one first coupling element which is configured to interact functionally with a first counter-coupling element provided on the first table subunit, so that by way thereof, the angle unit is releasably connected to the first table subunit.

Furthermore, the patient table can have further elements, for example, a table subframe, for example, in the form of a supporting column. This can also enable, in particular, an availability of the support surface in the horizontal and/or vertical plane or an inclination of a table subunit.

The support surface, provided at least by way of the first and second table subunit, the position of which relative to one another is fixed by the angle unit permits the positioning of the patient. Furthermore, further surface regions can also be provided, for example via further table subunits. The table subunits can also be designated table segments. Thereby, a first plane is assignable to the first surface region of the first table subunit and/or a second plane is assignable to the second surface region in which the first and/or second surface region is substantially provided and/or along which the surface regions of the table subunit are substantially oriented. This does not exclude, in particular, deviations of the first or second surface regions from a completely flat plane in the form, for example, of surfaces adapted to a body shape of a patient or from local depressions for the receiving of liquids, in particular bodily fluids.

The angle unit is thereby configured to fix the position of the first table subunit relative to the second table subunit and to secure the support surface against a change in the intersection angle on loading of the support surface by a patient. This means that in the state where the angle unit is connected to the first and second table subunits, the relative position of the first and second table subunits is fixed and substantially unchangeable in relation to unintended changes, in particular on a loading of the patient table with the patient. In particular, the support surface is secured by the angle unit against an unintended change of the intersection angle, so that the intersection angle is not or only insubstantially changed on a loading by a patient, but is substantially maintained. The angle unit can be configured to lock the intersection angle between the first and the second table subunits.

The angle unit can thus be configured for a large weight load and can have a material which has a sufficiently high stability and strength, so that also on a weight loading of the support surface, no or only an insignificant change of the intersection angle fixed by the angle unit takes place. The angle unit can, in particular, be configured rigid and not movable, by way of the intersection angle provided thereby.

The angle unit can, in particular, have a fiber composite material, plastic or metal, for example aluminum, or a combination thereof. Preferably, the angle unit has a material with a relatively high X-ray transparency, for example, a plastics or a carbon fiber material. Thereby, the use in the context of a medical imaging facility on the basis of X-ray radiation is particularly favorably possible, since an impairment of recorded X-ray images can be prevented as far as possible.

X-ray transparency should thereby be understood, in particular, to mean that the material preferably has a high level of transparency, i.e. a relatively low absorption coefficient, for X-ray radiation in the relevant energy region used, in particular, for medical X-ray imaging. For example, the medical X-ray imaging device is a C-arm X-ray device and the material is then preferably selected such that for X-ray energies which are used, typically, in conjunction with a C-arm X-ray device, only a relatively low absorption of the X-ray radiation relevant for the imaging occurs. The material can have, in particular, a substantially lower absorption coefficient for the X-ray energies used than iron and a lower absorption coefficient than aluminum. The material can, in particular, have a similar or lower absorption coefficient than carbon or than water.

The coupling element and the counter-coupling element are preferably configured to enable a positive-fitting and/or a non-positive-fitting connection, i.e. for a stable connection in relation to a patient loading. For example, the coupling element and the counter-coupling element can be configured as plug-in connections in the form of projections formed as pins or otherwise and as plug-in sockets in the form of pin receptacles or other cut-outs, which can be introduced into one another for a connection. The coupling element and counter-coupling element can be configured as a tongue-and-groove connection. The projections and corresponding receptacles are configured, in particular, for weight loading by a patient, in a suitable size and a suitable material.

In particular, the angle unit and at least the first table subunit is releasably connected, i.e. coupled, via the coupling element and the counter-coupling element. This means that the functional interaction between the first coupling element and the first counter-coupling element leads to a releasable connection of the angle unit and the first table subunit. Releasable can be understood in this context such that the connection is reversibly made and can also be released again. In particular, the connection can be made and released again multiple times and repeatedly. The connection can be released, in particular, non-destructively. Thereby, in embodiments of the invention, the releasable connection can be made and released again without an additional tool, i.e. manually. It is however also conceivable that the coupling element and the counter-coupling element can be released and connected with the aid of a tool. For example, this can be achieved via a closing mechanism in the form of a bolt or bar engaging in a recess, which can be moved via a key into and out of the recess.

The second table subunit can be connected to the angle unit firmly, i.e. not releasably without difficulty, or in one piece. This can mean that the angle unit and the second table subunit are only releasable destructively. In other embodiment variants, the second table subunit is also releasably connected to the angle unit.

Advantageously, via a releasable connection, the angle unit and the table unit can be released from and reattached to one another in a simple and time-efficient manner, so that for example, a first angle unit having a first intersection angle can also be replaced by a second angle unit which provides a second intersection angle. It is thereby made possible to combine different angle units with the first table subunit in a simple manner, so that a support surface adapted to an application case can be provided for the patient. The patient table according to the invention advantageously permits a modular construction, wherein at least one but preferably a plurality of different types of angle units and at least two, preferably more than two, table subunits, possibly different in shape and size can be combined into a respective patient table according to the invention. The invention thereby advantageously permits the support surface to be provided for different situations and for an optimum treatment or diagnosis.

The inventors have also discovered that for the provision of a possibility for an adaptable support surface within the patient supporting surface, i.e. a provision of the support surface in mutually intersecting planes, metal joints or metal frames which have sufficient stability against a change on loading do not necessarily have to be used. The inventors have discovered, however, that it is sufficient in order to provide a rigid fixing of the support surface in a desired position, but via at least one releasable connection, merely to implement a reversible fixing so that different positions of the support surface are enabled by way of the combination of different angle units with the table subunit or the table subunits.

The patient table according to at least one embodiment of the invention thus permits the use of materials more favorable for X-ray imaging than metal and also, where relevant, more economical materials without having to forego a flexible positioning of the patient.

The first table subunit, the second table subunit and the angle unit accordingly preferably have an X-ray-transparent material, i.e. essentially a material with a high X-ray transparency. The first table subunit, the second table subunit and the angle unit can thereby have the same material or respectively different materials. Preferably, materials are also used, the X-ray absorption of which substantially corresponds to that of a water-equivalent or which have a reduced X-ray absorption relative thereto. Preferably, materials are also used, the X-ray absorption of which substantially corresponds to that of plastics. A material that is used can be, for example, a carbon fiber material, a plastics material, for example polyurethane or polyethylene, or a carbon fiber-reinforced plastics material. Other suitable materials can also be used. A material used can also be a glass fiber-reinforced plastics material on the basis of epoxy resin, or similar.

In an advantageous variant embodiment of the patient table according to the invention, the angle unit has a second coupling element which is configured to interact functionally with a second counter-coupling element provided on the second table subunit, so that by way thereof, the angle unit is also releasably connected to the second table subunit.

A releasable connection both of the first table subunit and also of the second table subunit to the angle unit advantageously permits individual elements of the patient table to be implemented that are smaller in their dimensions and better to handle. In addition, a greater variety of combinations and an improved reusability of table subunits in combination with angle units are enabled. Overall thereby, a material-saving and space-saving embodiment of a modular patient table can be implemented. Furthermore, the use of different materials which are attuned to a different loading of the table subunits and the angle unit is thereby made possible more easily.

The second coupling element and the second counter-coupling element can thereby be configured similarly to the first coupling element and the first counter-coupling element. However, they can also be configured differently from one another.

According to an advantageous embodiment of the invention, the angle unit has a first portion along a first axis and a second portion along a second axis which intersects the first axis at the intersection angle, so that in the state where the angle unit is connected to the first and the second table subunits, the first plane of the first surface region is fixed parallel to the first axis and the second plane of the second surface region is fixed parallel to the second axis, so that the first plane and the second plane intersect one another at the intersection angle.

The angle unit defines the intersection angle by way of the first portion and the second portion. In this embodiment, the first portion and the second portion are configured, in particular, rigid and substantially unchangeable and unmovable relative to one another. In that the first table subunit is fixed parallel to the first axis and the second table subunit is fixed parallel to the second axis, i.e. secured against an unintended change in the position, the intersection angle is also locked between the planes of the first support surface and the second support surface. Such an embodiment represents a possibility for fixing the intersection angle that is particularly easy to provide.

In a further embodiment variant of the patient table, in the state where the angle unit is connected to the first and second table subunits, the angle unit provides a third surface region of the support surface for the patient, which is formed spatially between the first and the second surface regions.

The support surface typically has a first extent along a longitudinal axis of the patient table and, relative thereto, a shorter second extent along a transverse axis. In this embodiment variant, the third surface region then adjoins in the longitudinal direction on one side, the first surface region, and on the opposite side in the longitudinal direction, the second surface region.

The third surface region can be formed as a curved surface or an angled surface in the direction of the longitudinal axis between the first and the second surface regions, wherein the curvature of the surface of the third surface region is defined by the intersection angle.

The inventors have discovered that, in this way, an embodiment of the angle unit of particularly stable shape can be provided. This can advantageously also permit coupling elements of large-area construction to be provided along the sides facing one another between the respective table subunit and the angle unit, which provide a particularly high stability relative to a weight loading, wherein point loadings of locally delimited regions on the table subunit or the angle unit can be prevented. In this way, a continuous connected surface for the positioning of the patient can also be provided. Preferably, in this embodiment variant, the first, second and third surface regions form a flush adjoining support surface, wherein gaps and step-like transitions between the surface regions are prevented.

According to an advantageous variant embodiment of the invention, the first counter-coupling element is provided at least partially on one side of the first table subunit, which in the state where the angle unit is connected to the first and the second table subunits, is oriented parallel to the longitudinal axis and/or the second counter-coupling element is provided at least partially on one side of the second table subunit which, in the state where the angle unit is connected to the first and the second table subunits, is oriented parallel to the longitudinal axis.

The coupling and/or counter-coupling element is then configured accordingly on one abutting face of the table subunit or the angle unit which face one another in the connected state. Advantageously, coupling and/or counter-coupling elements on the sides of the patient table which could possibly lead to hindering of the clinical personnel can be avoided.

In a further advantageous variant embodiment of the invention, the first counter-coupling element is provided at least partially on one side of the first table subunit and/or the second counter-coupling element is provided at least partially on one side of the second table subunit which, in the state where the angle unit is connected to the first and the second table subunits, is oriented parallel to the transverse axis.

In this variant embodiment, the counter-coupling elements are provided laterally on the table subunit or table subunits which do not face one another in the connected state. This means that the angle unit is mounted, in particular, laterally on the patient table, for example as a plug-in locking. In this variant embodiment, the angle unit can advantageously be configured compacter and thereby permit a simpler handling and have a smaller space and material requirement.

Furthermore, a lateral placement of the angle unit can make it possible that if the patient table is used in combination with an X-ray imaging device, the angle unit is arranged only in an edge region or entirely outside an image recording region of the supported patient. Thereby, an extended material selection for the embodiment of the angle unit is available if relevant. For example, another type of plastic having greater stability but lower X-ray transparency than for the table subunits themselves can be used, which are preferably made of a material with a highest possible X-ray transparency. Influences interfering with the X-ray imaging in the form of edges and material transitions in the central imaging region can be reduced by a lateral arrangement.

Furthermore, embodiments of the patient table are also conceivable wherein both on the side parallel to the longitudinal direction and also on the side parallel to the transverse axis, a counter-coupling element to a corresponding coupling element of the angle unit or respective parts thereof are configured. These can, for example, fulfill different functions or take account of different loading directions.

According to a further advantageous embodiment of the invention, the first coupling element and/or the second coupling element has at least one projection or a cut-out, and the first counter-coupling element and/or the second counter-coupling element has at least one substantially complementarily formed counter-cut-out or a substantially complementarily formed counter-projection, which in the state where the angle unit is connected to the first and the second table subunits, engage with one another so that the position of the first table subunit and of the second table subunit is fixed relative to the angle unit.

Complementarily formed means, in particular, adapted to one another so that the at least one projection and the at least one counter-cut-out can be introduced into one another. In particular, these are configured to enable a positive-fitting and/or non-positive-fitting connection. In particular, they are configured in shape, size and material to ensure a stable connection and fixing with regard to a weight loading of the support surface by a patient.

In an advantageous embodiment, the at least one projection or the at least one cut-out is formed to be cylindrical, conical, domed or cuboid.

For example, a plurality of pin-like projections can be provided on the coupling element which are inserted into complementarily formed pin receptacles in the counter-coupling element laterally on the table subunits, in order to effect a fixing of the angle unit relative to the table subunit and a locking of the intersection angle.

According to a variant embodiment of the invention, the angle unit has at least one cut-out with a U-shaped profile. In the state where the angle unit is connected to the first and second table subunits, in each case, a part of the surface region of the first and second table subunits is introduced into the at least one U-shaped cut-out of the angle unit.

The cut-out can be configured as an elongated cut-out along the first axis in the first portion and along the second axis in the second portion of the angle unit as a continuously formed cut-out. A U-shaped cut-out can also be provided, respectively, on the first and on the second portion. The U-shaped profile then has the cut-out or the cut-outs in an intersection plane perpendicular to the first axis in the first portion and/or the second axis in the second portion. The first and/or second table subunit can be inserted into the cut-out to create the releasable connection. In the connected, i.e. inserted state, the angle unit at least partially overlaps the support surface of the patient formed by the surface region of the table subunit. The inserted region of the respective table subunit itself serves in this embodiment variant as a counter-coupling element and the U-shaped cut-out serves as a coupling element which interacts functionally with the counter-coupling element.

Advantageously, in this way a particularly simple and stable plug-in mechanism can be provided which itself suffices without additional projections or cut-outs as counter-coupling elements on the table subunits. Thus, a particularly simple cleaning of the individual parts can be enabled.

According to an optional variant embodiment of the invention, the patient table additionally has a joint element with a joint axis about which the first table subunit and/or the second table subunit, with the releasable connection between the angle unit and the first table subunit and the second table subunit released, is arranged to be rotatable.

The first and second table subunits are movably connected to one another via the joint element. The joint axis usually extends parallel to the transverse extent of the patient table. For the orientation of the table subunits relative to one another with regard to the intersection angle before a locking by the angle unit, the first and/or the second subunits can be rotated about the joint axis as far as the desired position. After the orientation, the angle unit can be connected to the first and the second table subunit and thus fix the intersection angle and ensure a stable support surface.

A joint element that is provided can thereby enable a simplified orientation of the first table subunit relative to the second table subunit with regard to an angle that is taken up. The inventors have discovered that the use of the angle unit as a fixing of the intersection angle in combination with a joint advantageously enables the selection of a material for the joint element which otherwise possibly does not have sufficient stability for a stable positioning of the patient. The joint element can in this case have a plastics material, instead of metal for example. This enables, in particular, the favorable use of the patient table according to the invention in combination with an X-ray imaging device without dispensing with the stable alignment of the support surface.

At least one embodiment of the invention further relates to a table subunit of a patient table with a support surface for a patient for use with other embodiments, having a counter-coupling element and configured to provide a surface region of the support surface.

The advantages of the patient table according to at least one embodiment of the invention and its variant embodiments described above are transferrable to the table subunit for use according to one of these embodiments.

At least one embodiment of the invention further relates to a patient table system comprising a patient table according to at least one embodiment of the invention in accordance with one of the aspects described. Furthermore, the patient table system comprises a positioning apparatus with a kinematic system for the relative positioning of the first and/or the second table subunits, wherein the positioning apparatus has at least one connecting element which is configured to interact functionally with a counter-connecting element on the first and/or second table subunit so that the positioning apparatus is releasably couplable to the first and/or second table subunit and wherein the positioning apparatus is configured in the state coupled to the first table subunit and/or the second table subunit to orient the first and the second table subunits relative to one another when the releasable connection between the angle unit and the first and/or the second table subunits is released.

The positioning apparatus is, in particular, releasably connectable to the first and/or second table subunits. This advantageously enables the mounting of the positioning apparatus for positioning the table subunits, the undertaking of a first orientation via the positioning apparatus, after the first orientation, fixing of the position of the table subunits relative to one another via the angle unit or locking of the intersection angle and subsequently releasing of the positioning apparatus again from the first and/or second table subunits. Thereby, the positioning apparatus can be mounted on the patient table and removed again, as required, so that X-ray sensitive materials and positioning apparatus that are suitable for undertaking an orientation of the table subunits can also be used.

The positioning apparatus thereby comprises, in particular, a kinematic system. The positioning apparatus can have traveling axes, actuators, motors or other positioning apparatuses, configured for the relative positioning of the table subunits. In particular, the positioning apparatus can be configured to be controllable via a control facility.

The control facility can comprise, for example, an input unit and a computer unit. For example, via the input unit, for example a keyboard, a target position can be specified by an operator, said target position being converted by the computer unit into control signals for the control of the positioning apparatus, for example, for the traveling axes and motors, and output thereto. The positioning apparatus can also comprise a sensor, for example, an optical or electronic sensor which can determine the current position of the table subunits and possibly can monitor the positioning result.

The computer system can be, in particular, a computer, a microcontroller or an integrated circuit. A computer unit may have hardware elements or software elements, for example, a microprocessor or a so-called FPGA (Field Programmable Gate Array).

It is possible for the positioning apparatus to be releasably coupled to merely one table subunit or to at least two table subunits simultaneously. The positioning apparatus can be configured to move one, two or more table subunits for an orientation via the positioning apparatus. For example, only the second table subunit is oriented via the positioning apparatus relative to a first table subunit which is stationary during the orientation.

The connecting elements can be formed complementarily to the counter-coupling element(s) of the respective table subunits. In this case, a counter-coupling element on a respective table subunit can correspond to the counter-connecting element of the positioning apparatus. However, differently configured counter-connecting elements can also be provided on the table subunits, and connecting elements corresponding thereto.

Advantageously, the clinical personnel and an efficient operational procedure can be supported via the positioning apparatus and a simple and, in particular, automated first orientation of the table subunits can be enabled.

At least one embodiment of the invention further relates to a medical imaging facility having an X-ray device and a patient table according to at least one embodiment of the invention, wherein the X-ray device has an X-ray source and an X-ray detector positioned in a beam path of the X-ray source and wherein at least a part of the support surface of the patient table is arranged within the beam path of the X-ray source.

The medical imaging facility can be, in particular, an X-ray imaging facility which is used for an operation with X-ray monitoring. The medical imaging facility is, for example, a C-arm X-ray device or similar. The medical imaging facility comprises an X-ray source, typically an X-ray tube, and an X-ray detector, wherein the X-ray detector is positioned in the beam path of the X-ray source and X-ray radiation is emitted from the X-ray source in the direction of the X-ray detector. For an X-ray image recording, the patient or the relevant recording region of the patient is positioned in the beam path of the X-ray source. In the case of a patient positioned on a patient table, at least a part of the patient table is accordingly also positioned within the beam path. Through the use of a patient table according to at least one embodiment of the invention, interfering influences from, for example, a metal joint or a restriction of the recording region due to a metal frame can be prevented and, at the same time, a support surface can be provided which can be set at different angles within the patient supporting surface, i.e. the support surface and thus permits an optimum positioning of the patient in the medical imaging facility, for example, for an operation.

At least one embodiment of the invention also relates to a medical imaging facility wherein the X-ray device is a C-arm X-ray device.

Figure 1:
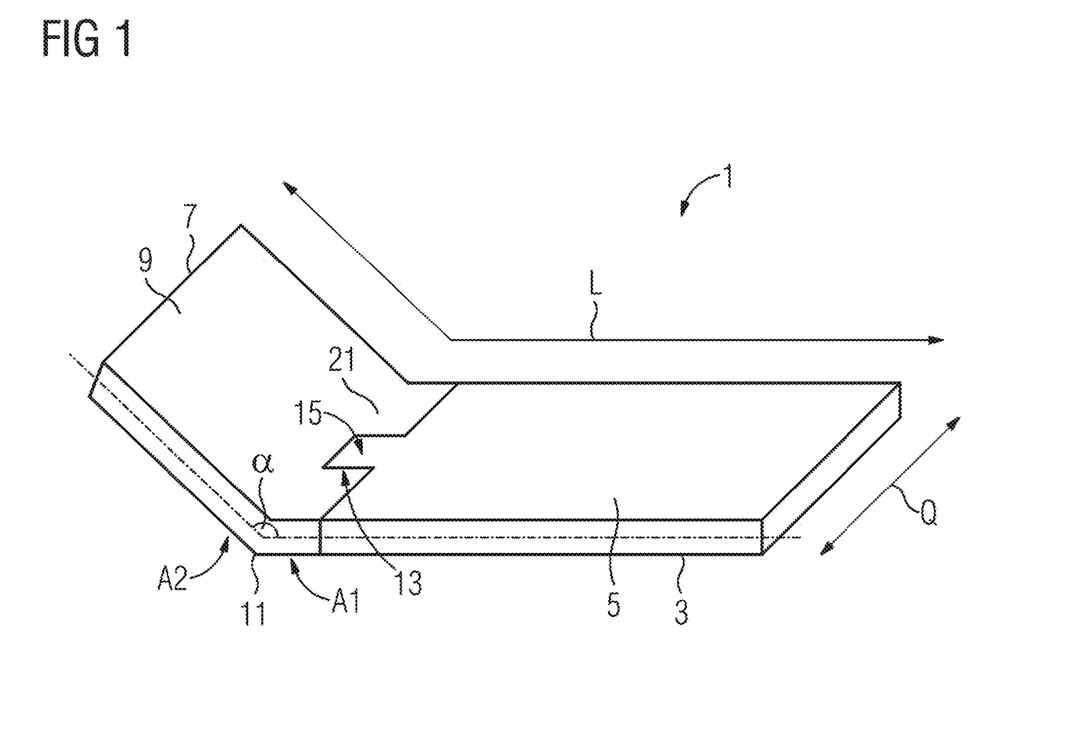
FIG. 1 shows a patient table with a support surface for a patient in a first embodiment.

FIG. 1 shows a patient table 1 with a support surface for a patient in a first embodiment. The patient table 1 comprises a first table subunit 3, configured to provide a first surface region 5 of the support surface, a second table subunit 7, configured to provide a second surface region 9 of the support surface. Furthermore, the patient table 1 has an angle unit 11, which in the example shown, is firmly connected to the second table subunit and, in particular, is configured in one piece with the second table subunit 7. The support surface of the patient table 1 thereby has a first extent L along a longitudinal axis of the patient table 1 and, relative thereto, a shorter, second extent Q along a transverse axis.

The patient table 1 can also have further elements, for example, a patient table subframe 41 which, however, in this representation and in the following figures are omitted.

The angle unit 11 is releasably connected to the first table subunit 3. This means that the angle unit 11 and the table subunit 3 can be repeatedly and, in particular, non-destructively released from one another and re-connected. For this purpose, the angle unit 11 comprises a first coupling element 13 which is configured to interact functionally with a first counter-coupling element 15 provided on the first table subunit 3, so that by way thereof, the angle unit 11 is releasably connected to the first table subunit 3.

In particular, the coupling element 13 and the counter-coupling element 15 enable a positive-fitting and/or non-positive-fitting connection of the angle unit to the first table subunit. The coupling element or the counter-coupling element can thereby be, for example, plug-in connections or plug-in receptacles in the form of projections or cut-outs which can be introduced into one another for forming the releasable connection, wherein they are configured for a weight loading of the patient table by a patient in a suitable size and a suitable material. The coupling element and counter-coupling element can be configured, for example, as a tongue-and-groove system.

The angle unit 11 is configured to fix the position of the first table subunit 3 relative to the second table subunit 7 such that the first surface region 5 is provided in a first plane and the second surface region 9 is provided in a second plane intersecting the first plane at an intersection angle α and such that the support surface is secured against a change in the intersection angle α on loading of the support surface by a patient 102.

For this purpose, the angle unit 11 shown has a first portion A1 along a first axis and a second portion A2 along a second axis intersecting the first axis at an intersection angle α. In the respectively connected state of the angle unit 11 to the first table subunit 3 and the second table subunit 7, the first plane of the first surface region 5 is fixed parallel to the first axis and the second plane of the second surface region 9 is fixed parallel to the second axis, so that the first plane in which the first table subunit 3 is positioned and the second plane in which the second table subunit 7 is positioned intersect one another at the intersection angle α.

The angle unit 11 is, in particular, configured to be rigid, i.e. the first portion A1 and the second portion A2 are configured substantially not movable relative to one another. This means that the intersection angle α of the angle unit 11 is configured substantially unchangeable at the angle unit 11. In particular, the embodiment of the angle unit 11 is selected to have a sufficiently high level of stability to ensure a rigid provision of the support surface, with regard to the intersection angle, and also on weight loading of the support surface by a patient. This means that the material and the design of the angle unit 11 is selected such that even on weight loading of the support surface by a patient 102 lying thereon, the intersection angle α between the first and the second planes is provided substantially unchanged. Furthermore, the angle unit 11, just like the table subunits, preferably has a material which is as X-ray-transparent as possible. A plastic or a carbon fiber composite is preferably selected as the material.

In the embodiment variant shown in FIG. 1, the angle unit 11 is provided on the second table subunit 7 such that the second table subunit 7 has a surface region 21 that is curved or angled in the direction of the longitudinal axis, the curvature of which is substantially determined by the intersection angle α. In this case, the angle unit 11 can also be described as formed spatially between the first surface region 5 and the second surface region 9 and as providing a third surface region 21 of the support surface for the patient 102.

In the embodiment shown in FIG. 1, the first counter-coupling element 13 is thereby configured at least partially on one side of the first table subunit 3 which in the state where the angle unit 11 is connected to the first table subunit 3 and the second table subunit 7 is oriented parallel to the longitudinal axis in the direction of the longitudinal extent L. This means that the coupling element 13 or the counter-coupling element 17 are configured on the sides facing one another in the connected state, i.e. the abutting faces of the angle unit 11 and the first table subunit 3.

The first table subunit 3, the second table subunit 7 which in this case is formed integrally with the angle unit 12, and the coupling element 15 or the counter-coupling element 13 are, in the case shown, also optionally configured such that a substantially step-free, level transition is provided between the individual regions of the support surface. This means that the units form a surface in the region of the support surface that is, as far as possible, flush-fitting.

Figure 2:
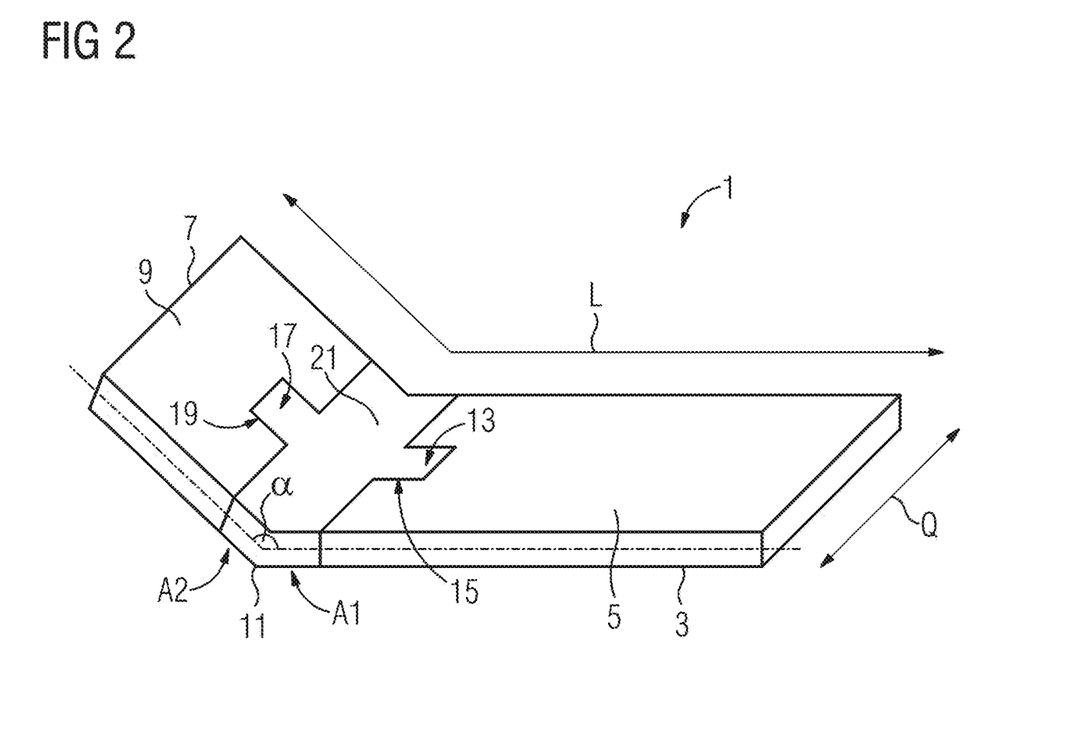
FIG. 2 shows a patient table with a support surface for a patient in a second embodiment.

FIG. 2 shows a second variant embodiment of a patient table 1 with a support surface for a patient 102. The variant embodiment differs from the embodiment shown in FIG. 1 primarily in that the angle unit 11 has a second coupling element 17 which is configured to interact functionally with a second counter-coupling element 19 provided on the second table subunit 7, so that by way thereof, the angle unit 11 is releasably connected, apart from the first table subunit 3, also to the second table subunit 7. This means that in this case, the angle unit 11 is releasably connected both to the first table subunit 3 and also to the second table subunit 7.

Advantageously, this variant embodiment allows, as compared with the variant embodiment shown in FIG. 1, subunits of the patient table 1 with smaller extents, which lead to an improved handling and can enable improved positioning. Similarly, a more flexible combination of angle units provided, with different intersection angles, and the table subunits provided is enabled.

Figure 3:
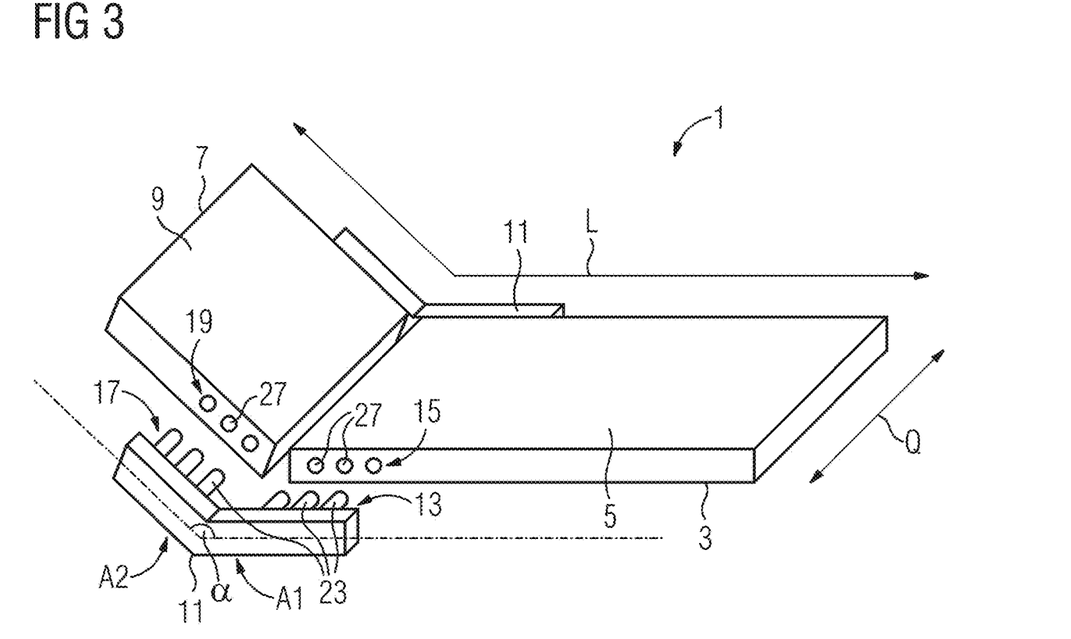
FIG. 3 shows a patient table with a support surface for a patient in a third embodiment.

FIG. 3 shows a further variant embodiment of a patient table 1 with a support surface for a patient 102.

In particular, in the embodiment shown, two angle units 11 are represented which are arrangeable laterally on the patient table 1, wherein one of the two angle units 11 represented is shown in a non-connected state, i.e. in a released state. The arrangement of two angle units 11 in this embodiment variant in place of a single angle unit can lead to an improved stability and a more secure fixing of the first and second table subunits. However, embodiments with only one angle unit on one of the sides are also conceivable.

The angle unit 11 or angle units 11 can be releasably connected both to the first and also to the second table subunit. The respective first counter-coupling element 15 is, as shown with the angle unit 11 released, respectively provided on one side of the first table subunit 3 and the respective second counter-coupling element 19 is respectively provided on one side of the second table subunit 7 which, in the state where the angle units 11 are connected to the first table subunit 3 and the second table subunit 7 is oriented parallel to the transverse axis Q of the patient table 1. In this example, the angle unit 11 is arranged laterally and externally to the projection of the support surface with the first table subunit 3 and the second table subunit 7.

In this embodiment variant also, the respective rigidly formed angle units 11 each have a first portion A1 along a first axis and a second portion A2 along a second axis intersecting the first axis at the intersection angle α. Thereby, the first and the second portions are configured unmovable and substantially unchangeable relative to one another. The intersection angle is then firmly defined by the first and the second portions. The angle unit 11 and the first table subunit 3 and the second table subunit 7 are couplable and fixable relative to one another, such that in the respective connected state of the angle unit 11 to the first table subunit 3 and the second table subunit 7, the first plane of the first surface region 5 is fixed parallel to the first axis and the second plane of the second surface region 9 is fixed parallel to the second axis, so that the first plane and the second plane of the surface regions of the support surface intersect one another at the intersection angle α. This means that the material and the design of the angle unit 11 is selected such that even on weight loading of the support surface by a patient 102 lying thereon, the intersection angle α between the first and the second planes is provided substantially unchanged.

In the embodiment variant of the patient table 1 and of the angle unit 11 as shown, the first coupling element 13 and the second coupling element 17 each have three projections 23 in the form of pins. The number and design of the projections is herein selected purely by way of example. The first counter-coupling element 15 and the second counter-coupling element 19 have counter-cut-outs 27 which are complementarily formed, in the case shown, essentially pin receptacles in the form of holes. In the state where the angle unit 11 is connected to the first table subunit 3 and the second table subunit 7, the projections 13 and the cut-outs 27 engage with one another, so that the respective positions of the first table subunit 3 and the second table subunit 7 relative to the angle unit 11 are fixed. In that the position of the angle unit 11 relative to the first table subunit 3 and the second table subunit 7 is fixed, the relative position of the first table subunit 3 and the second table subunit 7 is secured and fixed and the intersection angle α assumed by the planes of the first surface region 5 and the second surface region 9 to one another against an unintended change on loading by a patient 102 is locked. The angle element 11 serves in this case as a lateral plug-in locking which mechanically fixes the table subunits, which in the unconnected state are movable, relative to the intersection angle α.

The projections 23 or cut-outs 27 shown are configured substantially cylindrical in this case. Other configurations can also have, for example, conical, domed, pyramidal, cuboid or truncated cone-shaped cut-outs or projections. The shape and configuration of the cut-outs and projections are designed, in particular, in order to ensure the necessary stability for the fixing and positioning, even at a high weight loading of the support surface by a patient.

Figure 4:
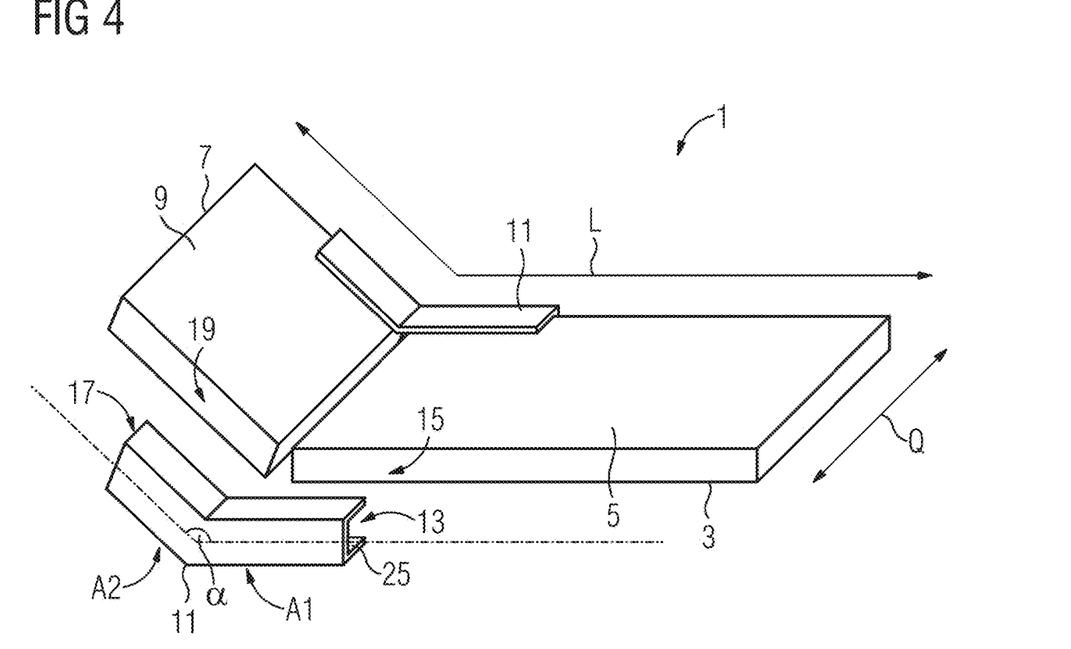
FIG. 4 shows a patient table with a support surface for a patient in a fourth embodiment.

FIG. 4 shows a fourth variant embodiment of a patient table 1 with a support surface for a patient 102 having a further embodiment variant of the angle unit 11.

In the representation, again, an angle unit 11 is shown in the connected state and an angle unit 11 is shown in the unconnected state. The angle unit 11 has two portions A1 and A2 intersecting at the intersection angle α, the orientation of which to one another is substantially unchangeable.

In this variant embodiment, the respective angle unit 11 has at least one cut-out 24 with a U-shaped profile. The cut-out 24 with the U-shaped profile can be provided continuous both on the first portion A1 of the angle unit 11 in the region of the first coupling element 13 and also on the second portion A2 of the angle unit 11 in the region of the second coupling element 17. A corresponding U-shaped cut-out 25 can also be provided on each portion. The U-shaped cut-out or cut-outs 25 is or are adapted to the design of the table subunits. In the state where the angle unit 11 is connected to the first table subunit 3 and the second table subunit 5, a part 15 of the first table subunit 3 or a part 19 of the second table subunit 7 which overlaps with the first surface region 5 and/or the second surface region 9 is introduced into the U-shaped cut-out 25. This means that, in this embodiment variant, the first counter-coupling element 15 or the second counter-coupling element 19 corresponds to the respective part of the first table subunit 3 or of the second table subunit 7 introducible into the U-shaped cut-out 24. In the connected state, the angle unit 11 then fixes the first and the second table subunits in their relative position in respect of a weight loading of the support surface.

It is therein conceivable that the first table subunit 3 and the second table subunit 7 narrow in the region introduced into the cut-out 24, i.e. in the case shown, are configured less high in the vertical direction so that a substantially flush ending in the region of the support surface and thus a substantially level, stepless support surface can be provided.

Figure 5:
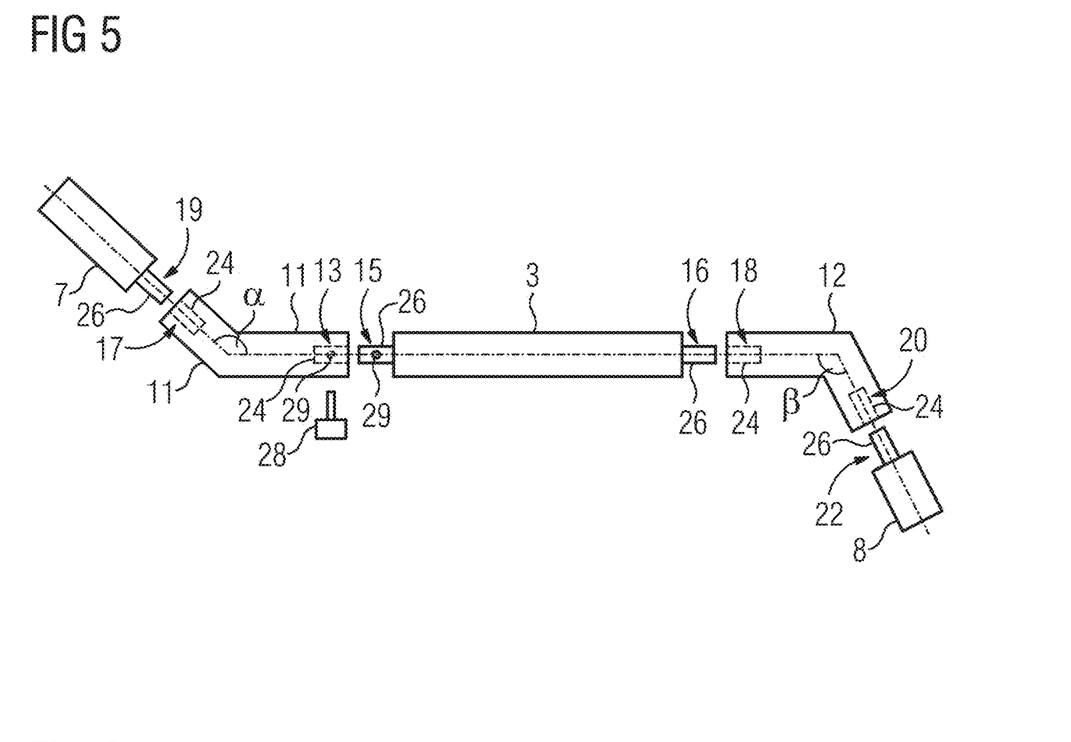
FIG. 5 shows a sectional view of a plurality of table subunits and angle units in an unconnected state for using as a patient table with a support surface for a patient.

FIG. 5 shows a sectional view of a first table subunit 3 for a patient table 1 with a support surface for a patient 102, in an unconnected state with an angle unit 11 and a second table subunit 7. In addition, a further angle unit 12 and a further table subunit 8 are provided. The first table subunit is positionable via the angle unit 11 relative to the second table subunit 7 at the intersection angle α specified by the angle unit and is fixable with respect to the intersection angle α. The further table subunit 8 is providable, via the further angle unit 12, relative to the first table subunit 7 at the intersection angle β given by the further angle unit 12 and possibly different from the intersection angle α.

The table subunits 3, 7, 8 and angle units 11, 12 are each releasably connectable via the corresponding coupling elements 13, 17, 18, 20 formed on the angle units and via the counter-coupling elements 15, 16, 19, 22 formed on the table subunits, wherein in this example embodiment, the coupling elements 13, 17, 18, 20 and counter-coupling elements 15, 16, 19, 22 are each formed as cut-outs 24 and substantially complementary projections 26 which are introduced into one another and engage with one another for the production of the releasable connections, so that a positive-fitting and/or non-positive-fitting connection is achieved.

For the use of the first table subunit with regard to a preferred modular construction patient table with the elements described here, in the example shown, the table subunits 7, 3, 8, the angle units 11, 12 and the coupling elements 17, 13, 18, 20 and counter-coupling elements 19, 15, 16, 22 are each configured such that the further angle unit 12 is also usable for the positioning of the first table subunit 3 to the second table subunit 7. In this case, the first table subunit 3 and the second table subunit 7 would then be locked accordingly at the angle β. This means that the angle units 11, 12 and the table subunits 7, 8 are interchangeably combinable with the first table subunit. A plurality of angle units can be available, providing different intersection angles so that the first table subunit is positionable at different angles relative to the second table subunit and/or further table subunits. Similarly, table subunits configured in many ways can be available, combinable in a modular manner with the first table subunit via angle units.

Such a modular construction is also executable with the other embodiments of the angle unit and the coupling elements than are shown explicitly in FIG. 5.

Furthermore, purely by way of example, an additional optional embodiment of the coupling element and/or the counter-coupling element with an additional fixing possibility is shown on the coupling element 13 and the counter-coupling element 15. In this case, the angle unit 11 has in the region of the cut-out of the coupling element 13 and the counter-coupling element 15 of the table subunit 3, in each case, a fixing cut-out 29 which in the state where the angle unit 11 is connected to the table subunit 3 overlap congruently, so that a fixing device 28 in the form of a fixing pin can be guided, i.e. inserted through or into the overlapping fixing cut-outs 29. Differently configured additional fixing possibilities on the coupling element or counter-coupling element or on the table subunits can also be provided, which can serve as additional securing mechanisms against an unintended loosening of the table subunits. For example, folding or sliding bars are conceivable which can be used for additional securing. For example, a clamping device can also be provided via a lever, wherein by operating the lever, a pulling force can be exerted on the angle unit in the direction toward the table subunit, which leads to a particularly secure connection of the elements and which can only be released by renewed operation.

Figure 6:
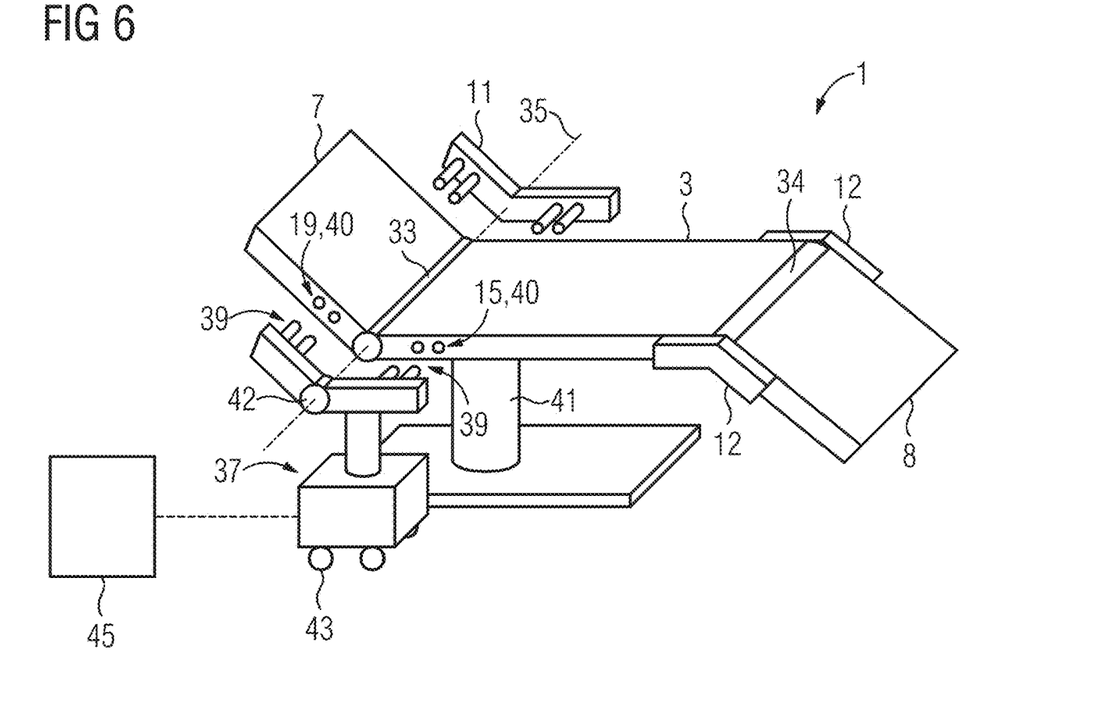
FIG. 6 shows a patient table system.

FIG. 6 shows a patient table system with a patient table 1 having a support surface for a patient 102. The patient table 1 of a patient table system according to the invention can be configured according to the example variant embodiments described above on the basis of FIGS. 1 to 5, or differently. In the example shown, the first and second table subunits are positionable relative to one another via the angle unit 11 in a similar form to that already described in relation to FIG. 3 via a plug-in locking to be mounted laterally, and lockable at the intersection angle α.

In addition to the variant embodiment shown in FIG. 3, in this embodiment, the patient table 1 additionally has a joint element 33 with a joint axis 35 about which the second table subunit 7 is arranged to be rotatable with the releasable connection between the angle unit 11 and the first table subunit 3 and the second table subunit 7 released. This means that provided the angle unit 11 is not connected to the first and second table subunits, the second table subunit 7 can be rotated about the joint axis 35 for aligning the table subunit relative to the first table subunit with regard to the intersection angle α. The joint element 33 thereby comprises in particular a material which is as X-ray-transparent as possible, in particular a plastics material. The joint element 33 can permit a simplified handling and alignment of the table subunits relative to one another before a locking of the intersection angle via the angle unit 11. The lack of mechanical stability of such a joint element 33 having an X-ray invisible material, in particular a joint element made of plastics, is then compensated for by the rigid plug-in locking via the angle unit 11.

Furthermore, apart from the first and the second table subunits, the patient table 1 described also comprises a third table subunit 8 which can be fixed relative to the first table subunit 3 via the further angle unit 12. Also arranged between the first table subunit 3 and the third table subunit 8 is a further joint element 32 made of an X-ray-transparent material, which enables a simple alignment of the further table subunit 8 with regard to the adopted intersection angle relative to the first table subunit 3.

The patient table 1 also has a table subframe 41 in the form of a supporting column. The table subframe 41 can also permit both an inclination of the first table subunit 3 and also a vertical and horizontal positioning of the support surface or the patient table as a whole.

Apart from a patient table 1 according to an embodiment of the invention, the patient table system also comprises a positioning apparatus 37 with a kinematic system for the relative positioning of the first table subunit 3 and the second table subunit 7 relative to one another. For this, the positioning apparatus 37 has connecting elements 39 which are configured for functional interaction with counter-connecting elements 40 on the first table subunit 3 and the second table subunit 7 so that the positioning apparatus is releasably couplable, i.e. releasably connectable, to the first table subunit 3 and the second table subunit 7. In the case shown, the connecting element 39 is configured identically or at least similarly, with regard to form, to the first or the second coupling element 13, 17 of the angle unit 11, so that the respective connecting element 39 is configured to interact functionally with the first and/or the second counter-coupling element 15, 19 of the first and the second table subunit so that the releasable coupling, i.e. connection, is creatable between the positioning apparatus 37 and the first and second table subunits via the connecting elements 39 and the counter-coupling elements 19, 15. This means that in this case, the counter-coupling elements 19, 15 represent the counter-connecting elements 40 for the positioning apparatus 37.

The positioning apparatus 37 is configured, in the coupled state and when the releasable connection between the angle unit 11 and the first and/or the second table subunit is released, i.e. in the case shown, when the plug-in locking by the angle unit 11 is released, to align the first table subunit 3 and the second table subunit 7 relative to one another. In the case shown, this means, in particular, that the positioning apparatus 37 is configured to align the second table subunit 7, on the basis of a rotation about the joint axis of a joint 42 of the positioning apparatus 37 relative to the first table subunit so that the first surface region 5 of the first table subunit 3 is provided, i.e. is oriented, in a first plane and the second surface region 9 is provided, i.e. is oriented, in a second plane intersecting the first plane at a pre-determined angle.

Furthermore, in other embodiments, positioning apparatuses 37 of more complex design are also conceivable which can position the second table subunit 7 vertically, horizontally and also with regard to the inclination of the provided surface region relative to the first table subunit 3. For this, the positioning apparatus 37 has, in particular, a kinematic system which is suitable to enable an alignment and positioning of the table subunits coupled to the positioning apparatus 37. In particular in embodiment variants, the kinematic system can comprise positioning apparatus in the sense of controllable traveling axes, actuators or motors which are controllable via a control facility 45, so that they can undertake, in an automated manner, an alignment of the table subunits into a target position, for example, a particular intersection angle specified by an operator. The target position can be input via an input unit comprised by the control facility 45, for example a keyboard.

Furthermore, the positioning apparatus 37 can comprise a sensor by which a current position of the table subunits can be determined and the positioning result can possibly be monitored. The control facility 45 can be comprised by the positioning apparatus 37 or, as in the case illustrated, can be connected, for example, by cable or radio to the positioning apparatus 37, wherein control signals can be output by the control facility for controlling the positioning apparatus. The positioning apparatus can be configured mobile, i.e. movable, as a whole. In the example shown, the positioning apparatus has rollers 43 so that the positioning apparatus can be easily moved to the patient table 1 and removed therefrom again. Similarly, a purely mechanical manually adjustable positioning apparatus is also conceivable.

After the initial alignment via the positioning apparatus 37, the relative position of the first table subunit 3 relative to the second table subunit 7 can be locked in that the angle unit 11 is releasably connected to the first and the second table subunits, so that the support surface is secured, i.e. locked, against a change in the intersection angle $\alpha$ on loading of the support surface by a patient 102. After the connection of the angle unit 11 to the first and the second table subunits, the positioning apparatus can be released again.

Figure 7:
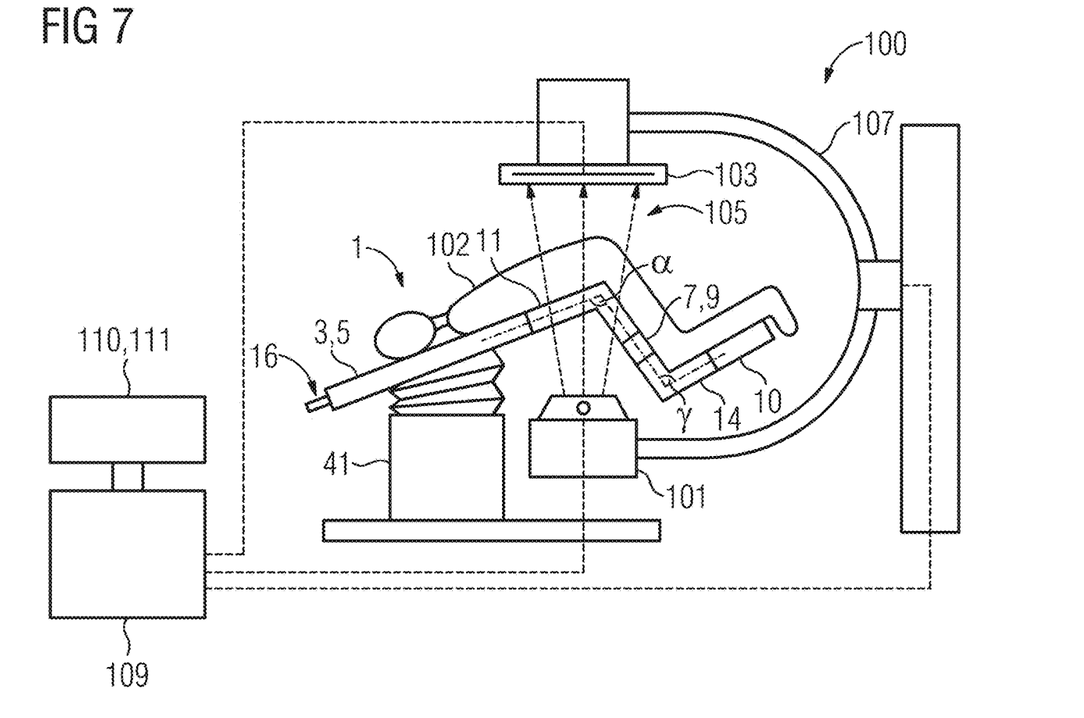
FIG. 7 shows a medical imaging facility.

In FIG. 7, a medical imaging facility 100, specifically a C-arm X-ray device, is shown by way of example. This has an X-ray source 101 which during operation of the X-ray device 100 emits X-ray radiation. The X-ray detector 103 is fastened in opposition to the X-ray source 101, i.e. in particular in the beam path 105 of the emitted X-ray radiation. The X-ray source 101 and the X-ray detector 103 are arranged movable relative to the patient table 1 via the C-arm 107. For the evaluation of the X-ray radiation acquired via the X-ray detector 103, the X-ray detector 103 is connected to a control computer 109, also known as an image processing computer. For control of the X-ray source 101 and of the C-arm 107, these are also connected to the control computer 109. Furthermore, the imaging facility can comprise an input and output unit, wherein an input and output unit comprises at least one input unit 110 and/or at least one output unit 111 which enables an interaction of an operator, for example, a control of the X-ray device with the imaging facility.

In the variant embodiment described here, the patient table 1 comprises a first table subunit 3, designed to provide a first surface region 5 of the support surface, a second table subunit 7, designed to provide a second surface region 9 of the support surface, and an angle unit 11 connected to the first and second table subunits, which is configured to fix the position of the first table subunit 3 relative to the second table subunit 7 such that the first surface region 5 is provided in a first plane and the second surface region 9 is provided in a second plane intersecting the first plane at an intersection angle $\alpha$ and such that the support surface is secured against a change in the intersection angle $\alpha$ on weight loading of the support surface by a patient 102 lying thereon. The angle unit 11 also comprises a first coupling element 13 that is not visible in this illustration which is configured to interact functionally with a first counter-coupling element 15 that is also not visible in this illustration and is provided on the first table subunit 3, so that by way thereof, the angle unit 11 is releasably connected to the first table subunit 3. In the variant embodiment of the patient table 1 shown here, the second table subunit 7 is also releasably connected to the angle unit 11. The patient table as shown here also has a further table subunit 10 which is releasably connected, via a further angle unit 14 at a further angle $\gamma$ which is possibly different from the intersection angle $\alpha$, to the second table subunit 7, so that the support surface can be provided for the patient 102 in the form of a modular system such that with it an optimum positioning of the patient 102 for the respective case can be achieved.

Furthermore, a second optional counter-coupling element 16 provided on the first table subunit 3 on the head side of the patient table 1 seen relative to the supported patient 102, allows a second angle unit 12 to be connected releasably, possibly beside the first angle unit 11, to the first table subunit 3 in order to provide the support surface of the patient table 1 possibly flexibly adaptable to another imaging situation or operation situation.

The patient table 1 further has a table subframe 41 which permits the support surface to be displaced possibly in the vertical and horizontal directions relative to the X-ray device 100. In the case shown, the table subframe is also configured to provide the table subunit 3 in a position inclined relative to the horizontal.

At least a part of the support surface with the patient is positioned, for the recording of X-ray images via the X-ray device 100, within the beam path 105 of the X-ray source 101 and between the X-ray source 105 and the X-ray detector 103. According to a particularly advantageous embodiment, the table subunits and angle units have a material that is as X-ray-transparent as possible, for example, a plastic, so that restrictions in the recording region of the X-ray images, or artifacts in the X-ray images are advantageously prevented.

The subject matter of the invention is not restricted to the above described example embodiments. Rather, further embodiments of the invention can be derived from the above description by persons skilled in the art. In particular, the individual features of the invention described on the basis of the different example embodiments and their embodiment variants can also be combined in another way.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A patient table including a support surface for a patient, the patient table comprising:
    a first table subunit, configured to provide a first surface region of the support surface;
    a second table subunit, configured to provide a second surface region of the support surface; and
    an angle unit having an intersection angle, the angle unit being rigid and not moveable about the intersection angle, the angle unit being configured to
        connect to the first table subunit,
        connect to the second table subunit, and
        fix a position of the first table subunit relative to the second table subunit, the first surface region being provided in a first plane and the second surface region being provided in a second plane, the second plane intersecting the first plane at the intersection angle, and
    the angle unit including at least
        a first coupling element, the first coupling element the configured to interact functionally with a first counter-coupling element the first table subunit, to releasably connect at least the angle unit to the first table subunit, and
        a second coupling element, the second coupling element configured to interact functionally with a second counter-coupling element on the second table subunit, to releasably connect the angle unit to the second table subunit.

2. The patient table of claim 1, wherein the angle unit includes
    a first portion along a first axis, and
    a second portion along a second axis, the second axis intersecting the first axis at the intersection angle, wherein, upon the angle unit connecting to the first table subunit and the angle unit connecting to the second table subunit,
        the first plane of the first surface region is fixed parallel to the first axis,
        the second plane of the second surface region is fixed parallel to the second axis, and
        the first plane intersects the second plane at the intersection angle.

3. The patient table of claim 2, wherein the support surface includes
    a first extent along a longitudinal axis of the patient table, wherein the second counter-coupling element is configured at least partially on one side of the second table subunit and the angle unit is configured to connect to the first able subunit and the second table subunit in an orientation parallel to the longitudinal axis, and
    a second extent along a transverse axis, the second extent being shorter than the first extent.

4. The patient table of claim 2, wherein the support surface includes
    a first extent along a longitudinal axis, and
    a second extent along a transverse axis, the second extent being shorter than the first extent, wherein the second counter-coupling element is provided at least partially on one side of the second table subunit, and the angle unit is configured to connect to the first table subunit and the second table subunit in an orientation parallel to the transverse axis.

5. The patient table of claim 2, wherein
    the first coupling element and the second coupling element includes at least one projection or at least one cut-out, and the second counter-coupling element includes at least one complementarily formed counter-cut-out or a complementarily formed counter-projection configured to connect with the at least one projection or the at least one cut-out, wherein, upon the angle unit connecting to the first table subunit and the angle unit connecting to the second table subunit, a position of the first table subunit is fixed relative to the angle unit and a position of the second table subunit is fixed relative to the angle unit.

6. The patient table of claim 2, wherein, upon the angle unit connecting to the first table subunit and the second table subunit, the angle unit is configured to provide a third surface region of the support surface for the patient, the third surface region the being formed spatially between the first surface region and the second surface region.

7. The patient table of claim 2, wherein the angle unit includes at least one cut-out with a U-shaped profile, configured to receive a part of a respective surface region of at least one of the first table subunit and the second table subunit.

8. The patient table of claim 2, further including
a joint element, connected to the first table subunit or to the second table subunit, and
a joint axis, wherein the first table subunit or the second table subunit are configured to be rotatable around the joint axis with the releasable connection between the angle unit and at least one of the first table subunit and the second table subunit being released.

9. The patient table of claim 1, wherein the support surface includes
a first extent along a longitudinal axis of the patient table, wherein the first counter-coupling element is configured at least partially on one side of the first table subunit, and the angle unit is configured to connect to the first table subunit and the second table subunit in an orientation parallel to the longitudinal axis, and
a second extent along a traverse axis, the second extent being shorter than the first extent.

10. The patient table of claim 1, wherein the support surface includes
a first extent along a longitudinal axis of the patient table, and
a second extent along a transverse axis, the second extent being sorter than the first extent, wherein the first counter-coupling element is provided at least partially on one side of the first table subunit and the angle unit is configured to connect to the first table subunit and the second table subunit in an orientation parallel to the transverse axis.

11. The patient table of claim 1, wherein
the first coupling element includes at least one projection or at least one cut-out, and
the first counter-coupling element includes at least one complementarily formed counter-cut-out or a complementarily formed counter-projection configured to connect with the at least one projection or the at least one cut-out, wherein, upon the angle unit connecting to the first table subunit and the angle unit connecting to the second table subunit, a position of the first table subunit is fixed relative to the angle unit and a position of the second table subunit is fixed relative to the angle unit.

12. The patient table of claim 11, wherein the at least one projection or the at least one cut-out is at least one of a cylindrical shape, a conical shape, a domed shape, or a cuboid shape.

13. The patient table of claim 1, wherein the angle unit includes at least one cut-out with a U-shaped profile, configured to receive a part of a respective surface region of at least one of the first table subunit and the second table subunit.

14. The patient table of claim 1, wherein the first table subunit, the second table subunit and the angle unit include an X-ray-transparent material.

15. The patient table of claim 1, the patient table further including
a joint element, connected to the first table subunit or to the second table subunit, and
a joint axis, wherein the first table subunit or the second table subunit are configured to be rotatable around the joint axis with the releasable connection between the angle unit and at least one of the first table subunit and the second table subunit released.

16. A patient table system, the patient table system comprising:
the patient table of claim 1; and
a positioning apparatus including a kinematic system for relative positioning of at least one of the first table subunit and the second table subunit, wherein
the positioning apparatus includes at least one connecting element, the at least one connecting element configured to interact functionally with a counter-connecting element on at least one of the first table subunit and the second table subunit to releasably couple the positioning apparatus to at least one of the first table subunit and the second table subunit, and
the positioning apparatus is configured to, upon coupling to at least one of the first table subunit and the second table subunit, align the first table subunit and the second table subunit relative to one another upon a releasable connection between the angle unit and at least one of the first table subunit and the second table subunit being released.

17. A medical imaging facility, comprising:
an X-ray device including
an X-ray source, and
an X-ray detector positioned in a beam path of the X-ray source; and
the patient table of claim 1, wherein at least part of the support surface of the patient table is arrange within the beam path of the X-ray source.

18. The medical imaging facility of claim 17, wherein the X-ray device is a C-arm X-ray device.

19. A patient table including a support surface for a patient, the patient table comprising:
a first table subunit, configured to provide a first surface region of the support surface;
a second table subunit, configured to provide a second surface region of the support surface; and
an angle unit, the angle unit being configured to
connect to the first table subunit,
connect to the second table subunit,
fix a position of the first table subunit relative to the second table subunit, the first surface region being provided in the first plane and the second surface region being provided in a second plane, the second plane intersecting the first plane at an intersection angle, and the support surface being secured against a change of the intersection angle upon loading of the support surface by the patient, and
provide a third surface region of the support surface upon the angle unit connecting to the first table subunit and the angle unit connecting to the second table subunit, the third surface region being formed spatially between the first surface region and the second surface region, and the angle unit including at least
- a first coupling element, the first coupling element configured to interact functionally with a first counter-coupling element on the first table subunit, to releasably connect at least the angle unit to the first table subunit.

20. The patient table of claim 19, wherein the angle unit includes
- a first portion along a first axis, and
- a second portion along a second axis, the second axis intersecting the first axis at the intersection angle, wherein, upon the angle unit connecting to the first table subunit and the angle unit connecting the second table subunit,
  - the first plane of the first surface region is fixed parallel to the first axis,
  - the second plane of the second surface region is fixed parallel to the second axis, and
  - the first plane intersects the second plane at the intersection angle.

21. The patient table of claim 19, wherein upon the angle unit connecting to the first table subunit and the angle unit connecting to the second table subunit, the angle unit is configured to provide a third surface region of the support surface for the patient, the third surface region being formed spatially between the first surface region and the second surface region.

22. A patient table including a support surface for a patient for use with a positioning apparatus, the patient table comprising:
- a first table subunit, configured to provide a first surface region of the support surface, the first table subunit having a first counter-coupling element configured to interact functionally with a first coupling element on the positioning apparatus; and
- a second table subunit, configured to provide a second surface region of the support surface, the second table subunit having a second-counter coupling element configured to interact functionally with a second coupling element on the positioning apparatus, wherein the positioning apparatus, upon coupling to at least one of the first table subunit and the second table subunit, is configured to align the first table subunit relative to the second table subunit, the first surface region of the aligned first table subunit being provided in a first plane and the second surface region of the aligned second table subunit being provided in a second plane, the first plane intersecting the second plane at an intersection angle; and
- an angle unit, the angle unit including at least
  - a third coupling element, the third coupling element configured to act functionally with the first counter-coupling element on the first table subunit, to releasably connect at least the angle unit to the first table subunit, and
  - a fourth coupling element, the fourth coupling element configured to interact functionally with the second counter-coupling element on the second table subunit, to releasably connect the angle unit to the second table subunit, wherein the angle unit, upon coupling to the first table subunit and the second table subunit, is configured to fix the aligned first table subunit relative to the aligned second table subunit at the intersection angle, the fixed first table subunit and the fixed second table subunit being secured against a change in the interaction angle upon loading of the support surface by the patient.

* * * * *